United States Patent
Parker (10) Patent No.: US 11,090,502 B2
(45) Date of Patent: *Aug. 17, 2021

(54) SYSTEMS AND METHODS FOR EXTENDING THE LIFE OF AN IMPLANTED PULSE GENERATOR BATTERY

(71) Applicant: Nevro Corp., Redwood City, CA (US)

(72) Inventor: Jon Parker, San Jose, CA (US)

(73) Assignee: Nevro Corp., Redwood City, CA (US)

( * ) Notice: Subject to any disclaimer, the term of this patent is extended or adjusted under 35 U.S.C. 154(b) by 168 days.

This patent is subject to a terminal disclaimer.

(21) Appl. No.: 15/884,202

(22) Filed: Jan. 30, 2018

(65) Prior Publication Data

US 2018/0221671 A1    Aug. 9, 2018

Related U.S. Application Data

(63) Continuation of application No. 14/887,251, filed on Oct. 19, 2015, now Pat. No. 9,884,198.

(60) Provisional application No. 62/067,408, filed on Oct. 22, 2014.

(51) Int. Cl.
| | | |
|---|---|---|
| A61N 1/37 | (2006.01) | |
| A61N 1/378 | (2006.01) | |
| A61N 1/372 | (2006.01) | |
| A61N 1/36 | (2006.01) | |

(52) U.S. Cl.
CPC ........ *A61N 1/3787* (2013.01); *A61N 1/36071* (2013.01); *A61N 1/37217* (2013.01)

(58) Field of Classification Search
CPC ................ A61N 1/378–3787; H02J 9/00–005
See application file for complete search history.

(56) References Cited

U.S. PATENT DOCUMENTS

| | | |
|---|---|---|
| 3,871,382 A | 3/1975 | Mann |
| 4,071,032 A | 1/1978 | Schulman |
| 4,082,097 A | 4/1978 | Mann et al. |

(Continued)

FOREIGN PATENT DOCUMENTS

| | | |
|---|---|---|
| EP | 0754437 | 1/1997 |
| EP | 1610437 | 12/2005 |

(Continued)

OTHER PUBLICATIONS

Supplementary European Search Report for European Patent Application No. 15853009, Applicant: Nevro Corp., dated May 15, 2018, 5 pages.

(Continued)

*Primary Examiner* — Eric D. Bertram
(74) *Attorney, Agent, or Firm* — Perkins Coie LLP (57) ABSTRACT

Systems and methods for extending the life of an implanted pulse generator battery are disclosed. A representative method for establishing charge parameters for a battery-powered implantable medical device includes receiving a patient-specific therapy signal parameter and, based at least in part on the patient-specific therapy signal parameter, determining a discharge rate for a battery of the implanted medical device. The method can further include determining a therapy run time, based at least in part on the discharge rate. The method can still further include determining at least one battery charging parameter, based at least in part on the run time.

7 Claims, 7 Drawing Sheets

(56) References Cited

U.S. PATENT DOCUMENTS

| | | |
|---|---|---|
| D250,719 S | 1/1979 | Jacobson et al. |
| 4,197,850 A | 4/1980 | Schulman et al. |
| 4,230,121 A | 10/1980 | Stanton |
| 4,441,498 A | 4/1984 | Nordling |
| D280,930 S | 10/1985 | Speicher et al. |
| 4,632,117 A | 12/1986 | James |
| 4,890,616 A | 1/1990 | Pinckaers |
| 5,065,083 A | 11/1991 | Owens |
| 5,144,946 A | 9/1992 | Weinberg et al. |
| D337,820 S | 7/1993 | Hooper et al. |
| 5,279,292 A | 1/1994 | Baumann et al. |
| D343,901 S | 2/1994 | Anderson |
| 5,591,212 A | 1/1997 | Keimel |
| 5,733,313 A | 3/1998 | Barreras, Sr. et al. |
| 5,755,743 A | 5/1998 | Volvz et al. |
| 5,769,877 A | 6/1998 | Barreras, Sr. |
| 5,807,397 A | 9/1998 | Barreras |
| 5,928,272 A | 7/1999 | Adkins et al. |
| 5,954,758 A | 9/1999 | Peckham et al. |
| 6,026,328 A | 2/2000 | Peckham et al. |
| 6,076,018 A | 6/2000 | Sturman et al. |
| 6,115,634 A | 9/2000 | Donders et al. |
| 6,167,303 A | 12/2000 | Thompson |
| 6,185,452 B1 | 2/2001 | Schulman et al. |
| 6,185,454 B1 | 2/2001 | Thompson |
| 6,223,080 B1 | 4/2001 | Thompson |
| 6,236,888 B1 | 5/2001 | Thompson |
| 6,323,603 B1 | 11/2001 | Persson |
| 6,324,426 B1 | 11/2001 | Thompson |
| 6,387,332 B1 | 5/2002 | Dickinson |
| 6,434,425 B1 | 8/2002 | Thompson |
| 6,453,198 B1 | 9/2002 | Torgerson et al. |
| 6,472,991 B1 | 10/2002 | Schulman et al. |
| 6,496,729 B2 | 12/2002 | Thompson |
| 6,553,263 B1 | 4/2003 | Meadows et al. |
| D478,990 S | 8/2003 | Kroll |
| 6,650,943 B1 | 11/2003 | Whitehurst et al. |
| 6,712,772 B2 | 3/2004 | Cohen et al. |
| 6,757,561 B2 | 6/2004 | Rubin et al. |
| 6,812,708 B2 | 11/2004 | Bristol |
| 6,871,099 B1 | 3/2005 | Whitehurst et al. |
| 6,909,915 B2 | 6/2005 | Greatbatch |
| 7,027,860 B2 | 4/2006 | Bruninga et al. |
| 7,054,689 B1 | 5/2006 | Whitehurst et al. |
| D523,144 S | 6/2006 | Wenger et al. |
| 7,120,499 B2 | 10/2006 | Thrope et al. |
| 7,127,288 B2 | 10/2006 | Sturman et al. |
| 7,142,923 B2 | 11/2006 | North et al. |
| 7,167,749 B2 | 1/2007 | Biggs et al. |
| 7,167,756 B1 | 1/2007 | Torgerson et al. |
| 7,177,703 B2 | 2/2007 | Boveja et al. |
| 7,184,836 B1 | 2/2007 | Meadows et al. |
| 7,209,792 B1 | 4/2007 | Parramon et al. |
| 7,254,449 B2 | 8/2007 | Karunasiri |
| 7,263,405 B2 | 8/2007 | Boveja et al. |
| D559,987 S | 1/2008 | Strother et al. |
| 7,330,762 B2 | 2/2008 | Boveja et al. |
| 7,337,010 B2 | 2/2008 | Howard et al. |
| 7,437,193 B2 | 10/2008 | Parramon et al. |
| 7,444,184 B2 | 10/2008 | Boveja et al. |
| 7,489,968 B1 | 2/2009 | Alexander |
| 7,496,404 B2 | 2/2009 | Meadows et al. |
| 7,571,002 B2 | 8/2009 | Thrope et al. |
| 7,606,622 B2 | 10/2009 | Reeve |
| 7,616,990 B2 | 11/2009 | Chavan et al. |
| 7,620,454 B2 | 11/2009 | Dinsmoor et al. |
| 7,636,602 B2 | 12/2009 | Baru Fassio et al. |
| 7,641,992 B2 | 1/2010 | Howard et al. |
| 7,650,191 B1 | 1/2010 | Lim et al. |
| D610,261 S | 2/2010 | Strother et al. |
| 7,682,745 B2 | 3/2010 | Howard et al. |
| 7,697,984 B2 | 4/2010 | Hill et al. |
| 7,769,442 B2 | 8/2010 | Shafer |
| 7,769,462 B2 | 8/2010 | Meadows et al. |
| 7,801,601 B2 | 9/2010 | Maschino et al. |
| 7,801,615 B2 | 9/2010 | Meadows et al. |
| 7,818,068 B2 | 10/2010 | Meadows et al. |
| 7,848,812 B2 | 12/2010 | Crowley |
| 7,865,245 B2 | 1/2011 | Torgerson et al. |
| 7,879,495 B2 | 2/2011 | Howard et al. |
| 7,894,905 B2 | 2/2011 | Pless |
| 7,916,013 B2 | 3/2011 | Stevenson |
| 7,941,220 B2 | 5/2011 | Tobacman |
| 8,128,600 B2 | 3/2012 | Gill |
| 8,190,259 B1 | 5/2012 | Smith et al. |
| D663,035 S | 7/2012 | Smith |
| D665,086 S | 8/2012 | Smith |
| D665,087 S | 8/2012 | Smith |
| 8,355,797 B2 | 1/2013 | Caparso et al. |
| 8,571,679 B2 | 10/2013 | Parramon et al. |
| 8,929,986 B2 | 1/2015 | Parker |
| 8,965,514 B2 | 2/2015 | Bikson et al. |
| 9,061,152 B2 | 6/2015 | Shi et al. |
| 9,192,769 B2 | 11/2015 | Donofrio et al. |
| 9,227,076 B2 | 1/2016 | Sharma et al. |
| 9,409,020 B2 | 8/2016 | Parker |
| 9,466,997 B2 | 10/2016 | Silva |
| 9,884,198 B2 | 2/2018 | Parker et al. |
| 2002/0035385 A1 | 3/2002 | Deziz |
| 2002/0068956 A1* | 6/2002 | Bloemer .............. A61N 1/378 607/1 |
| 2002/0107554 A1 | 8/2002 | Biggs et al. |
| 2002/0193844 A1 | 12/2002 | Michelson et al. |
| 2003/0114899 A1 | 6/2003 | Woods et al. |
| 2003/0135241 A1 | 7/2003 | Leonard et al. |
| 2003/0191504 A1 | 10/2003 | Meadows et al. |
| 2003/0195581 A1 | 10/2003 | Meadows et al. |
| 2003/0204222 A1 | 10/2003 | Leinders et al. |
| 2003/0208244 A1 | 11/2003 | Stein et al. |
| 2004/0034393 A1 | 2/2004 | Hansen et al. |
| 2004/0098060 A1 | 5/2004 | Ternes |
| 2004/0215287 A1 | 10/2004 | Swoyer et al. |
| 2004/0225333 A1 | 11/2004 | Greatbatch |
| 2005/0025480 A1 | 2/2005 | Yeh |
| 2005/0075695 A1* | 4/2005 | Schommer .......... A61N 1/3787 607/61 |
| 2005/0131467 A1 | 6/2005 | Boveja |
| 2005/0131483 A1 | 6/2005 | Zhao |
| 2005/0131486 A1 | 6/2005 | Boveja et al. |
| 2005/0131487 A1 | 6/2005 | Boveja et al. |
| 2005/0137644 A1 | 6/2005 | Boveja et al. |
| 2005/0143787 A1 | 6/2005 | Boveja et al. |
| 2005/0149146 A1 | 7/2005 | Boveja et al. |
| 2005/0154425 A1 | 7/2005 | Boveja et al. |
| 2005/0154426 A1 | 7/2005 | Boveja et al. |
| 2005/0165458 A1 | 7/2005 | Boveja et al. |
| 2005/0174098 A1 | 8/2005 | Watanabe |
| 2005/0178372 A1 | 8/2005 | Kesler et al. |
| 2005/0187590 A1 | 8/2005 | Boveja et al. |
| 2005/0197678 A1 | 9/2005 | Boveja et al. |
| 2005/0203583 A1 | 9/2005 | Twetan |
| 2005/0203584 A1 | 9/2005 | Twetan et al. |
| 2005/0216070 A1 | 9/2005 | Boveja et al. |
| 2005/0266301 A1 | 12/2005 | Smith et al. |
| 2005/0267546 A1 | 12/2005 | Parramon et al. |
| 2006/0004422 A1 | 1/2006 | De Ridder |
| 2006/0122655 A1* | 6/2006 | Greatbatch .......... A61N 1/378 607/33 |
| 2006/0224208 A1 | 10/2006 | Naviaux |
| 2007/0060955 A1 | 3/2007 | Strother et al. |
| 2007/0060968 A1 | 3/2007 | Strother et al. |
| 2007/0060980 A1 | 3/2007 | Strother et al. |
| 2007/0111587 A1 | 5/2007 | Ries et al. |
| 2007/0129768 A1 | 6/2007 | He |
| 2007/0213783 A1 | 9/2007 | Pless |
| 2007/0265489 A1 | 11/2007 | Fowler et al. |
| 2007/0270916 A1 | 11/2007 | Fischell et al. |
| 2008/0015644 A1 | 1/2008 | Julian |
| 2008/0039904 A1 | 2/2008 | Bulkes et al. |
| 2008/0058901 A1 | 3/2008 | Ternes et al. |
| 2008/0065182 A1 | 3/2008 | Strother et al. |
| 2008/0077184 A1 | 3/2008 | Denker et al. |
| 2008/0097554 A1 | 4/2008 | Payne et al. |
| 2008/0125833 A1 | 5/2008 | Bradley et al. |

(56) References Cited

U.S. PATENT DOCUMENTS

| | | |
|---|---|---|
| 2008/0129225 A1 | 6/2008 | Yamamoto et al. |
| 2008/0132926 A1 | 6/2008 | Eichmann et al. |
| 2008/0156333 A1 | 7/2008 | Galpern et al. |
| 2008/0216846 A1 | 9/2008 | Levin |
| 2008/0255631 A1 | 10/2008 | Sjostedt et al. |
| 2008/0262563 A1 | 10/2008 | Sjostedt |
| 2008/0294219 A1 | 11/2008 | Osypka et al. |
| 2008/0319441 A1 | 12/2008 | Seid |
| 2009/0012576 A1 | 1/2009 | Erbstoeszer et al. |
| 2009/0017700 A1 | 1/2009 | Zart et al. |
| 2009/0018600 A1 | 1/2009 | Deininger et al. |
| 2009/0018607 A1 | 1/2009 | Crowley et al. |
| 2009/0132010 A1 | 5/2009 | Kronberg |
| 2009/0157142 A1 | 6/2009 | Cauller |
| 2009/0204119 A1 | 8/2009 | Bleich et al. |
| 2009/0204173 A1 | 8/2009 | Fang et al. |
| 2009/0210029 A1 | 8/2009 | Tsui |
| 2009/0228074 A1 | 9/2009 | Edgell et al. |
| 2009/0248094 A1 | 10/2009 | McDonald |
| 2009/0248118 A1 | 10/2009 | Bradley et al. |
| 2009/0270948 A1 | 10/2009 | Nghiem et al. |
| 2009/0281596 A1 | 11/2009 | King et al. |
| 2009/0281599 A1 | 11/2009 | Thacker et al. |
| 2010/0004654 A1 | 1/2010 | Schmitz et al. |
| 2010/0010567 A1 | 1/2010 | Deem et al. |
| 2010/0038132 A1 | 2/2010 | Kinney et al. |
| 2010/0049275 A1 | 2/2010 | Chavan et al. |
| 2010/0094115 A1 | 4/2010 | Pond, Jr. et al. |
| 2010/0094231 A1 | 4/2010 | Bleich et al. |
| 2010/0106223 A1 | 4/2010 | Grevious et al. |
| 2010/0137943 A1 | 6/2010 | Zhu |
| 2010/0137944 A1 | 6/2010 | Zhu |
| 2010/0144281 A1 | 6/2010 | Kim et al. |
| 2010/0144283 A1 | 6/2010 | Curcio et al. |
| 2010/0168818 A1 | 7/2010 | Barror et al. |
| 2010/0233896 A1 | 9/2010 | Dilmaghanian |
| 2010/0274314 A1 | 10/2010 | Alataris |
| 2010/0274317 A1 | 10/2010 | Parker et al. |
| 2010/0305631 A1 | 12/2010 | Bradley et al. |
| 2010/0305663 A1 | 12/2010 | Aghassian |
| 2010/0324570 A1 | 12/2010 | Rooney et al. |
| 2011/0054583 A1 | 3/2011 | Litt et al. |
| 2011/0060282 A1* | 3/2011 | Dogwiler .......... A61M 5/14244 604/151 |
| 2011/0071593 A1 | 3/2011 | Parker et al. |
| 2011/0112601 A1 | 5/2011 | Meadows et al. |
| 2011/0112609 A1 | 5/2011 | Peterson |
| 2011/0112610 A1 | 5/2011 | Rahman et al. |
| 2011/0118661 A1 | 5/2011 | Pless et al. |
| 2011/0144468 A1 | 6/2011 | Boggs et al. |
| 2011/0224710 A1 | 9/2011 | Bleich |
| 2011/0245708 A1 | 10/2011 | Finkel et al. |
| 2011/0270363 A1 | 11/2011 | Schramm |
| 2012/0095744 A1 | 4/2012 | Rahman |
| 2012/0101551 A1 | 4/2012 | Aghassian et al. |
| 2012/0253440 A1 | 10/2012 | Grohmann |
| 2012/0315798 A1 | 12/2012 | Poon et al. |
| 2013/0035740 A1 | 2/2013 | Sharma |
| 2013/0066399 A1 | 3/2013 | Min |
| 2013/0066411 A1 | 3/2013 | Thacker et al. |
| 2013/0238048 A1* | 9/2013 | Almendinger ....... A61N 1/3787 607/40 |
| 2014/0217291 A1 | 8/2014 | Deutscher |
| 2014/0277268 A1 | 9/2014 | Lee |
| 2015/0005842 A1 | 1/2015 | Lee |
| 2015/0039047 A1 | 2/2015 | Parker |
| 2015/0039048 A1 | 2/2015 | Woods |
| 2015/0088227 A1 | 3/2015 | Shishilla et al. |
| 2016/0114171 A1 | 4/2016 | Parker |
| 2016/0256696 A1 | 9/2016 | Sharma |
| 2017/0036023 A1 | 2/2017 | Parker |
| 2019/0341803 A1 | 11/2019 | Cook |

FOREIGN PATENT DOCUMENTS

| | | |
|---|---|---|
| EP | 2243510 | 10/2010 |
| JP | 2002090196 | 3/2002 |
| WO | WO-2008121110 | 10/2008 |
| WO | WO-2011094074 A1 | 8/2011 |
| WO | WO-2012054234 | 4/2012 |

OTHER PUBLICATIONS

Gainer et al., "Use of the Peripheral Nerve Stimulator and Standard, Unsheathed Needles in Performing Regional Nerve Blocks," CRNA: The Clinical Forum for Nurse Anesthetists, vol. 3, No. 4, Nov. 1992, 4 pages.

Holst et al., "Nervous Control of Pancreatic exocrine secretion in pigs," Acta, Physiol. Scan 1979, 105, 19 pages.

Huxely et al., "Excitation and Conduction in Nerve: Quantitative Analysis," Science, Sep. 11, 1964; 145: 1154-9.

International Search Report and Written Opinion for International Patent Application No. PCT/US15/56275, Applicant: Nevro Corp., dated Jan. 14, 2016, 7 pages.

Klein, "Continuous Peripheral Nerve Blocks," Anesthesiology, vol. 103, No. 5, Nov. 2005, 3 pages.

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

Linderoth et al., "Mechanisms of Spinal Cord Stimulation in Painful Syndromes: Role of Animal Models," Pain Medicine, vol. 7, No. S1, 2006, 13 pages.

Mediati, R.D., , Mechanisms of Spinal Cord Stimulation, Florence Oct. 2, 2002.

North et al., "Spinal Cord Stimulation for Axial Low Back Pain," SPINE, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

Paterson CA et al., "Determinants of Occurrence and Volume of Transpyloric Flow During Gastric Emptying of Liquids in Dogs: Importance of Vagal Input," Dig Dis Sci, 2000, 45: 1509-1516.

Vadalouca et al., "Therapeutic Management of Chronic Neuropathic Pain: An Examination of Pharmacologic Treatment," Annals New York Academy of Sciences, 2006, pp. 164-186.

* cited by examiner

SYSTEMS AND METHODS FOR EXTENDING THE LIFE OF AN IMPLANTED PULSE GENERATOR BATTERY

CROSS-REFERENCE TO RELATED APPLICATION

The present application is a continuation of U.S. patent application Ser. No. 14/887,251, now issued as U.S. Pat. No. 9,884,198, filed Oct. 19, 2015, which claims priority to U.S. Provisional Application 62/067,408, filed on Oct. 22, 2014 and incorporated herein by reference.

TECHNICAL FIELD

The present technology is directed generally to systems and methods for extending the life of an implanted pulse generator battery. Particular embodiments include using patient-specific and/or battery-specific characteristics to tailor the parameters in accordance with which the battery of an implantable impulse generator is charged and/or discharged.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

Figure 1:
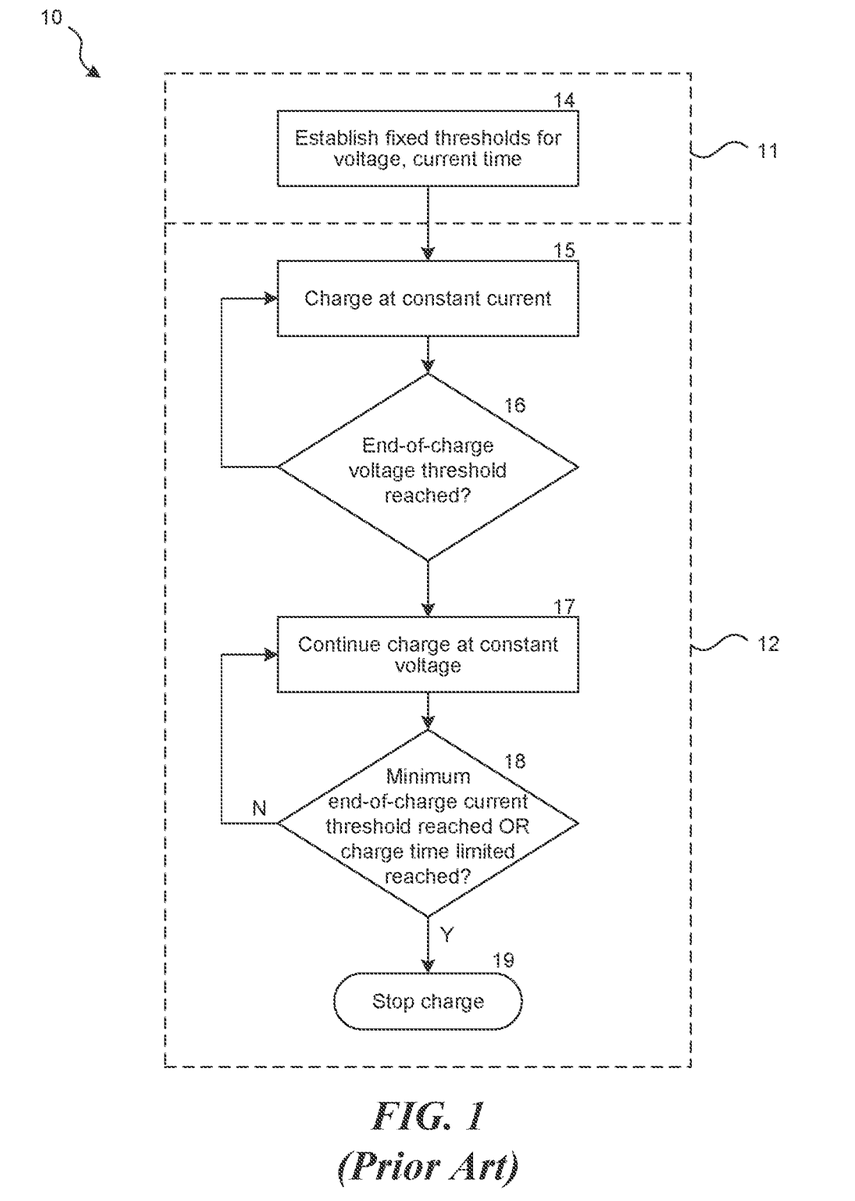
FIG. 1 is a flow diagram of a representative charging process in accordance with the prior art.

Conventional implanted SCS pulse generators are typically charged using a set of fixed charging parameters. FIG. 1 illustrates a representative process 10 in accordance with the prior art for establishing and using battery charging parameters for standard implantable pulse generators. The process includes a pre-charge parameter selection process 11 and a charging process 12. The pre-charge parameter selection process 11 includes establishing fixed thresholds for charging parameters, including thresholds for charging voltage levels and/or charging current levels, and time limits for one or more phases of the charging process 12 (block 14). The charging process 12 itself includes an initial period during which the battery is charged at a constant current (block 15). At block 16, the process includes determining whether an end-of-charge voltage threshold has been reached. If the voltage threshold has not been reached, then the battery is further charged using the constant current value. If the voltage threshold has been reached, then in block 17, the battery is further charged at a constant voltage level, rather than a constant current level. In block 18, the charger determines whether a minimum end-of-charge current threshold has been reached or, alternatively, whether a charging time limit has been reached. If either condition is met, the charging process stops (block 19). If the relevant condition is not met, the constant voltage phase of the charging process continues until the current threshold or time limit has been reached.

In contrast to traditional or conventional (i.e., paresthesia-based) SCS, a form of paresthesia-free SCS has been developed that uses therapy signal parameters that treat the patient's sensation of pain without generating paresthesia or otherwise using paresthesia to mask the patient's sensation of pain. One of several advantages of paresthesia-free SCS therapy systems is that they eliminate the need for uncomfortable paresthesias, which many patients find objectionable. However, a challenge with paresthesia-free SCS therapy systems is that the signal may be delivered at frequencies, amplitudes, and/or pulse widths that use more power than conventional SCS systems. As a result, the battery of the implanted system can discharge and become depleted at an accelerated rate. Accordingly, a follow-on challenge with providing non-paresthesia-generating spinal cord stimulation via an implanted pulse generator is that, in at least some cases, it may be difficult to maintain an effective signal as the charge available from the pulse generator battery decreases. One approach to power consumption challenges in the context of conventional SCS systems is to increase the frequency with which the pulse generator is charged, but this can be inconvenient for the patient. Another approach is to add signal conditioning hardware, for example, to boost the voltage provided by the battery as the battery discharges. A drawback with this approach is that it can be inefficient. Accordingly, there remains a need for effective and efficient therapy signal delivery, despite the possibility of increased power consumption resulting from the signal delivery parameters used for paresthesia-free patient therapy.

DETAILED DESCRIPTION

The present technology is directed generally to systems and methods for extending the life of an implanted pulse generator battery, which is used to deliver electrical signals (also referred to herein as "therapy signals") to provide patient treatment via spinal cord stimulation (SCS) or other techniques. For example, in one embodiment, the present technology includes establishing charge parameters for the battery of the pulse generator (or other implantable medical device) using patient-specific therapy signal parameters to establish a discharge rate for the battery, a therapy run time for the battery, and/or one or more associated battery charging parameters. Accordingly, the technology can tailor the battery charging parameters based on a particular patient's therapy parameters. In further embodiments, the technique can also include accounting for patient-specific charging habits and/or battery-specific parameters (e.g., the age of the battery and/or the number of times the battery has previously been charged). In any of these embodiments, the foregoing techniques can increase the life of the battery in a manner that is tailored to the specific manner in which the battery is used. In still further embodiments, methods in accordance with the present technology can be used to charge or discharge the battery in preparation for an extended period of storage. These techniques can increase the shelf life of the battery.

General aspects of the environments in which the disclosed technology operates are described below under Heading 1.0 ("Overview") with reference to FIGS. 2A and 2B. Particular embodiments of the technology are described further under Heading 2.0 ("Representative Embodiments") with reference to FIGS. 3-6. Additional embodiments are described under Heading 3.0 ("Additional Embodiments"). While the present technology is described in the environment of SCS, one with skill in the art would recognize that one or more aspects of the present technology are applicable to other, non-SCS implantable devices; e.g., more generally, implantable neurostimulators for treatment of one or more patient indications.

1.0 Overview

One example of a paresthesia-free SCS therapy system is a "high frequency" SCS system. High frequency SCS systems can inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.5 kHz to about 100 kHz) is occasionally referred to herein as "high frequency stimulation," "high frequency SCS," and/or "high frequency modulation." Further examples of paresthesia-free SCS systems are described in U.S. Patent Publication Nos. 2009/0204173 and 2010/0274314, the respective disclosures of which are herein incorporated by reference in their entireties.

Figure 2A:
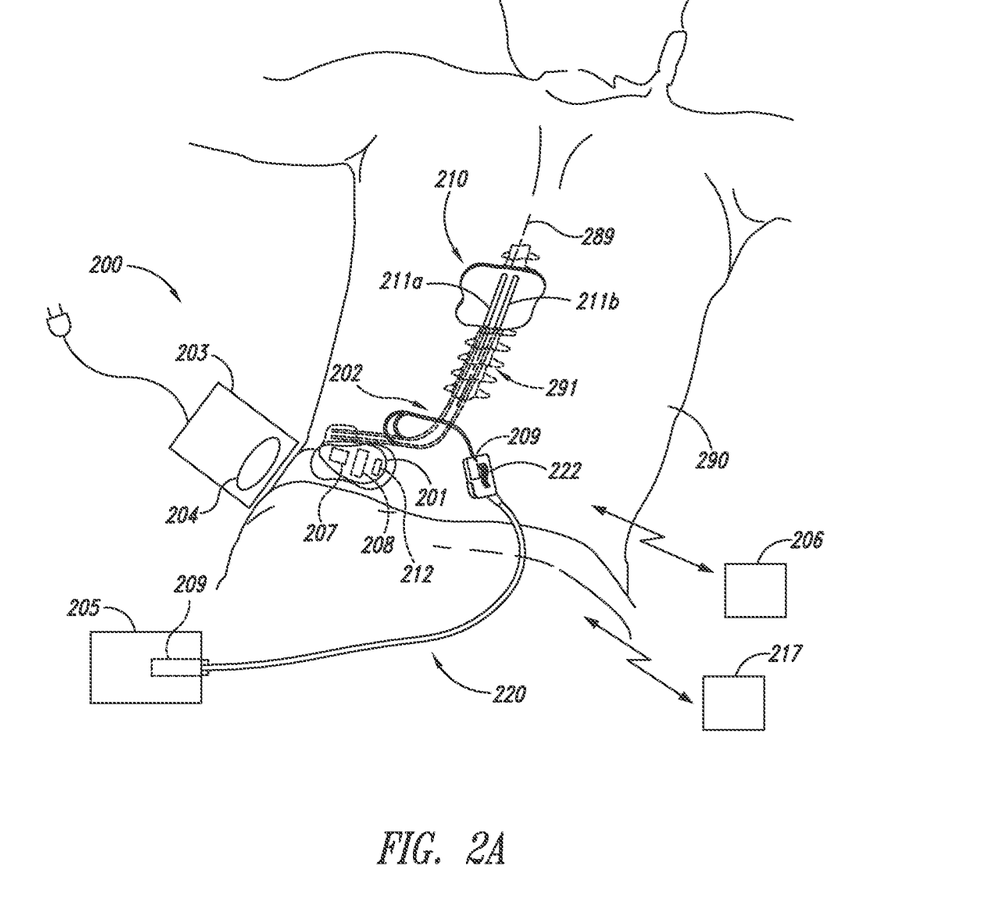
FIG. 2A is a partially schematic illustration of an implantable spinal cord modulation system positioned at the spine to deliver therapeutic signals in accordance with several embodiments in the present technology.

FIG. 2A schematically illustrates a representative patient therapy system 200 for providing relief from chronic pain and/or other conditions, arranged relative to the general anatomy of a patient's spinal column 291. The system 200 can include a signal generator 201 (e.g., an implanted or implantable pulse generator or IPG), which may be implanted subcutaneously within a patient 290 and coupled to one or more signal delivery elements or devices 210. The signal delivery elements or devices 210 may be implanted within the patient 290, typically at or near the patient's spinal cord midline 289. The signal delivery elements 210 carry features for delivering therapy to the patient 290 after implantation. The signal generator 201 can be connected directly to the signal delivery devices 210, or it can be coupled to the signal delivery devices 210 via a signal link or lead extension 202. In a further representative embodiment, the signal delivery devices 210 can include one or more elongated lead(s) or lead body or bodies 211 (identified individually as a first lead 211a and a second lead 211b). As used herein, the terms signal delivery device, lead, and/or lead body include any of a number of suitable substrates and/or support members that carry electrodes/devices for providing therapy signals to the patient 290. For example, the lead or leads 211 can include one or more electrodes or electrical contacts that direct electrical signals into the patient's tissue, e.g., to provide for therapeutic relief. In other embodiments, the signal delivery elements 210 can include structures other than a lead body (e.g., a paddle) that also direct electrical signals and/or other types of signals to the patient 290.

In a representative embodiment, one signal delivery device may be implanted on one side of the spinal cord midline 289, and a second signal delivery device may be implanted on the other side of the spinal cord midline 289. For example, the first and second leads 211a, 211b shown in FIG. 2A may be positioned just off the spinal cord midline 289 (e.g., about 1 mm offset) in opposing lateral directions so that the two leads 211a, 211b are spaced apart from each other by about 2 mm. In particular embodiments, the leads 211 may be implanted at a vertebral level ranging from, for example, about T8 to about T12. In other embodiments, one or more signal delivery devices can be implanted at other vertebral levels, e.g., as disclosed in U.S. Patent Application Publication No. 2013/0066411, which is incorporated herein by reference in its entirety.

The signal generator 201 can transmit signals (e.g., electrical signals) to the signal delivery elements 210 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 201 can include a machine-readable (e.g., computer-readable) or controller-readable medium containing instructions for generating and transmitting suitable therapy signals. The signal generator 201 and/or other elements of the system 200 can include one or more processor(s) 207, memory unit(s) 208, and/or input/output device(s) 212. Accordingly, the process of providing modulation signals, providing guidance information for positioning the signal delivery devices 210, establishing battery charging and/or discharging parameters, and/or executing other associated functions can be performed by computer-executable instructions contained by, on or in computer-readable media located at the pulse generator 201 and/or other system components. Further, the pulse generator 201 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 3-6 below. The dedicated hardware, firmware, and/or software also serve as "means for" performing the methods, processes, and/or sub-processes described herein. The signal generator 201 can also include multiple portions, elements, and/or subsystems (e.g., for directing signals in accordance with multiple signal delivery parameters), carried in a single housing, as shown in FIG. 2A, or in multiple housings.

The signal generator 201 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 212 shown schematically in FIG. 2A for purposes of illustration) that are carried by the signal generator 201 and/or distributed outside the signal generator 201 (e.g., at other patient locations) while still communicating with the signal generator 201. The sensors and/or other input devices 212 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 201 and/or signal delivery devices 210 can obtain power to generate the therapy signals from an external power source 203. In one embodiment, for example, the external power source 203 can by-pass an implanted signal generator and generate a therapy signal directly at the signal delivery devices 210 (or via signal relay components). The external power source 203 can transmit power to the implanted signal generator 201 and/or directly to the signal delivery devices 210 using electromagnetic induction (e.g., RF signals). For example, the external power source 203 can include an external coil 204 that communicates with a corresponding internal coil (not shown) within the implantable signal generator 201, signal delivery devices 210, and/or a power relay component (not shown). The external power source 203 can be portable for ease of use.

In another embodiment, the signal generator 201 can obtain the power to generate therapy signals from an internal power source, in addition to or in lieu of the external power source 203. For example, the implanted signal generator 201 can include a non-rechargeable battery or a rechargeable battery to provide such power. When the internal power source includes a rechargeable battery, the external power source 203 can be used to recharge the battery. The external power source 203 can in turn be recharged from a suitable power source (e.g., conventional wall power).

During at least some procedures, an external stimulator or trial modulator 205 can be coupled to the signal delivery elements 210 during an initial procedure, prior to implanting the signal generator 201. For example, a practitioner (e.g., a physician and/or a company representative) can use the trial modulator 205 to vary the modulation parameters provided to the signal delivery elements 210 in real time, and select optimal or particularly efficacious parameters. These parameters can include the location from which the electrical signals are emitted, as well as the characteristics of the electrical signals provided to the signal delivery devices 210. In some embodiments, input is collected via the external stimulator or trial modulator and can be used by the clinician to help determine what parameters to vary. In a typical process, the practitioner uses a cable assembly 220 to temporarily connect the trial modulator 205 to the signal delivery device 210. The practitioner can test the efficacy of the signal delivery devices 210 in an initial position. The practitioner can then disconnect the cable assembly 220 (e.g., at a connector 222), reposition the signal delivery devices 210, and reapply the electrical signals. This process can be performed iteratively until the practitioner obtains the desired position for the signal delivery devices 210. Optionally, the practitioner may move the partially implanted signal delivery devices 210 without disconnecting the cable assembly 220. Furthermore, in some embodiments, the iterative process of repositioning the signal delivery devices 210 and/or varying the therapy parameters may not be performed.

The signal generator 201, the lead extension 202, the trial modulator 205 and/or the connector 222 can each include a receiving element 209. Accordingly, the receiving elements 209 can be patient implantable elements, or the receiving elements 209 can be integral with an external patient treatment element, device or component (e.g., the trial modulator 205 and/or the connector 222). The receiving elements 209 can be configured to facilitate a simple coupling and decoupling procedure between the signal delivery devices 210, the lead extension 202, the pulse generator 201, the trial modulator 205 and/or the connector 222. The receiving elements 209 can be at least generally similar in structure and function to those described in U.S. Patent Application Publication No. 2011/0071593, incorporated by reference herein in its entirety.

After the signal delivery elements 210 are implanted, the patient 290 can receive therapy via signals generated by the trial modulator 205, generally for a limited period of time. During this time, the patient wears the cable assembly 220 and the trial modulator 205 outside the body. Assuming the trial therapy is effective or shows the promise of being effective, the practitioner then replaces the trial modulator 205 with the implanted signal generator 201, and programs the signal generator 201 with therapy programs selected based on the experience gained during the trial period. Optionally, the practitioner can also replace the signal delivery elements 210. Once the implantable signal generator 201 has been positioned within the patient 290, the therapy programs provided by the signal generator 201 can still be updated remotely via a wireless physician's programmer (e.g., a physician's laptop, a physician's remote or remote device, etc.) 217 and/or a wireless patient programmer 206 (e.g., a patient's laptop, patient's remote or remote device, etc.). Generally, the patient 290 has control over fewer parameters than does the practitioner. For example, the capability of the patient programmer 206 may be limited to starting and/or stopping the signal generator 201, and/or adjusting the signal amplitude. The patient programmer 206 may be configured to accept pain relief input as well as other variables, such as medication use.

In any of the foregoing embodiments, the parameters in accordance with which the signal generator 201 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication Nos. 2010/0274314; 2009/0204173; and 2013/0066411 (all previously incorporated by reference) and U.S. Patent Application Publication No. 2010/0274317, which is incorporated herein by reference in its entirety.

Figure 2B:
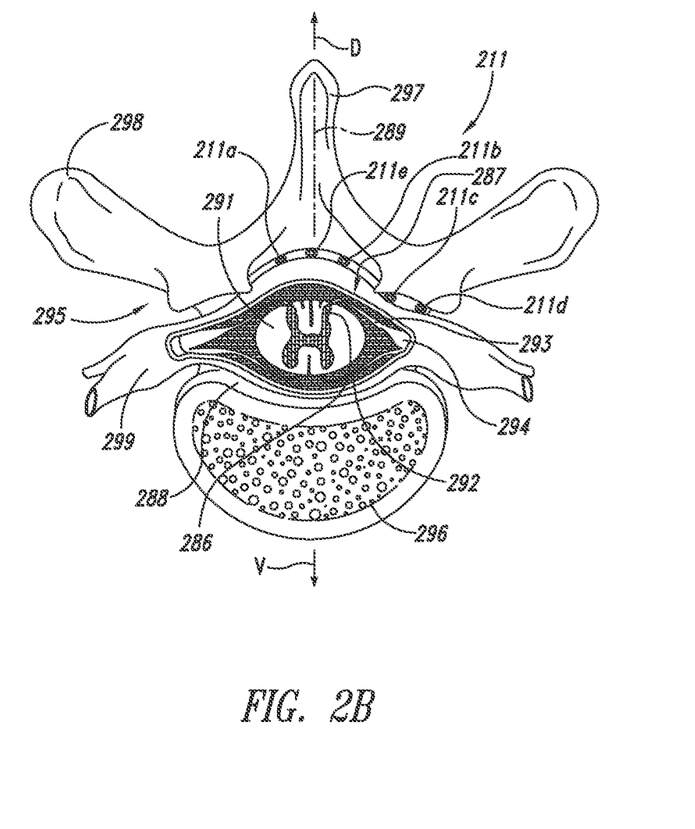
FIG. 2B is a partially schematic, cross-sectional illustration of a patient's spine, illustrating representative locations for implanted lead bodies in accordance with embodiments of the present technology.

FIG. 2B is a cross-sectional illustration of the spinal cord 291 and an adjacent vertebra 295 (based generally on information from Crossman and Neary, "Neuroanatomy," 1995 (published by Churchill Livingstone)), along with multiple leads 211 (shown as leads 211a-211e) implanted at representative locations. For purposes of illustration, multiple leads 211 are shown in FIG. 2B implanted in a single patient. In actual use, any given patient will likely receive fewer than all the leads 211 shown in FIG. 2B.

The spinal cord 291 is situated within a vertebral foramen 288, between a ventrally located ventral body 296 and a dorsally located transverse process 298 and spinous process 297. Arrows V and D identify the ventral and dorsal directions, respectively. The spinal cord 291 itself is located within the dura mater 299, which also surrounds portions of the nerves exiting the spinal cord 291, including the ventral roots 292, dorsal roots 293 and dorsal root ganglia 294. The dorsal roots 293 enter the spinal cord 291 at the dorsal root entry zone 287, and communicate with dorsal horn neurons located at the dorsal horn 286. In one embodiment, the first and second leads 211a, 211b are positioned just off the spinal cord midline 289 (e.g., about 1 mm. offset) in opposing lateral directions so that the two leads 211a, 211b are spaced apart from each other by about 2 mm, as discussed above. In other embodiments, a lead or pairs of leads can be positioned at other locations, e.g., toward the outer edge of the dorsal root entry zone 287 as shown by a third lead 211c, or at the dorsal root ganglia 294, as shown by a fourth lead 211d, or approximately at the spinal cord midline 289, as shown by a fifth lead 211e.

2.0 Representative Embodiments

Systems of the type described above with reference to FIGS. 2A-2B can include implanted pulse generators (IPGs) having rechargeable batteries or other rechargeable power sources that are periodically recharged with an external charger. Over the course of a given therapeutic regimen, the patient and/or the practitioner may change the parameters in accordance with which the electrical signals are delivered to the patient. As the parameters change, the rate at which electrical current is drawn or drained from the battery can also change. In addition, different patients may charge their batteries in accordance with different schedules, and/or may vary in the consistency with which they adhere to such schedules. Still further, the characteristics of the rechargeable battery can change over the course of time. For example, the overall charge capacity of the battery will typically decrease over time, e.g., due to chemical degradation. Techniques in accordance with the present technology, described further below, can tailor the manner in which the battery is charged and/or discharged by taking into account one or more of the foregoing variables to increase the usable life of the battery.

Figure 3:
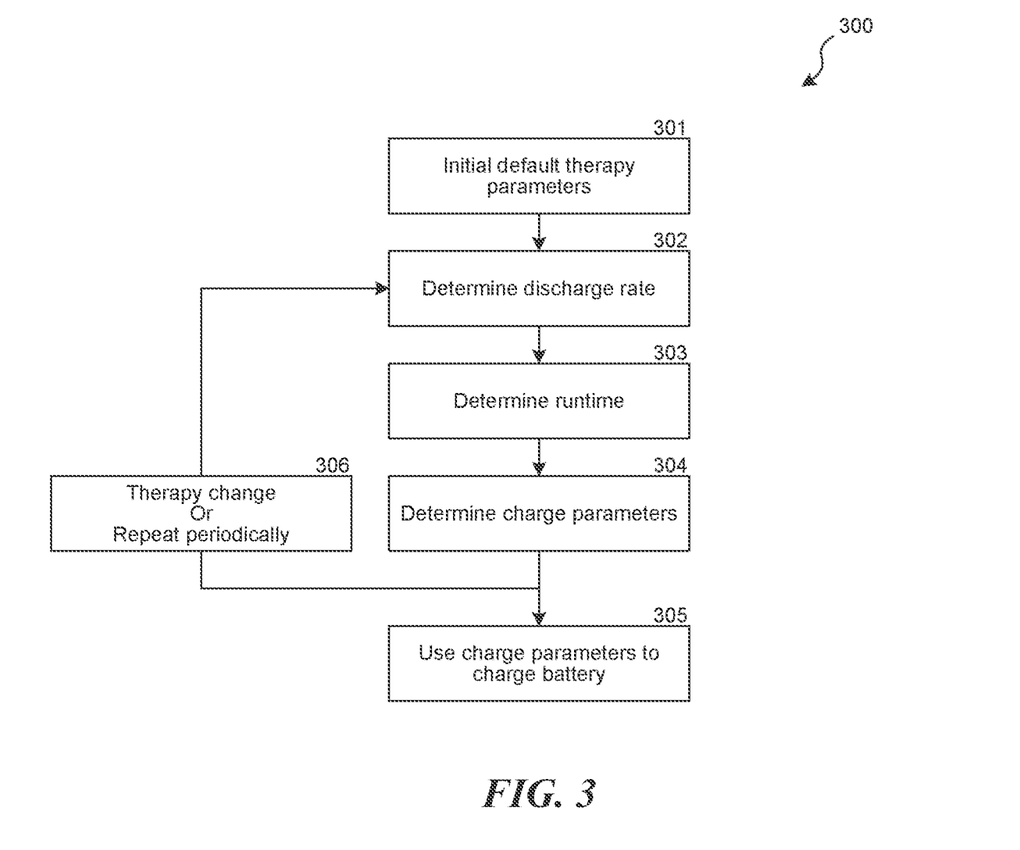
FIG. 3 is a flow diagram illustrating a representative process for establishing and using battery charge parameters in accordance with an embodiment of the present technology.

FIG. 3 is a flow diagram illustrating an overall process 300 configured in accordance with an embodiment of the present technology. Block 301 includes setting, reestablishing, identifying and/or obtaining initial and/or default therapy signal parameters. The therapy signal parameters can include the frequency, pulse width, inter-pulse interval, amplitude, duty cycle and/or any other suitable parameters of the therapy signal that may affect the rate at which the signal uses energy or charge provided by the battery of the implantable medical device as the signal is applied to the patient. In block 302, the rate at which the battery is discharged is calculated, estimated, or otherwise determined based at least in part on one or more of the therapy parameters identified in block 301. As used herein, the phrase "based at least in part" refers to a determination that is based on the identified parameter(s), with or without being based on an additional factor or factors. In block 303, the run-time for the IPG (based on a single charge) is determined, based at least in part on the discharge rate calculated at block 302. Accordingly, high discharge rates will produce shorter run-times and low discharge rates will produce longer run-times. At block 304, the process 300 includes setting, establishing, identifying or otherwise determining suitable battery charge parameters, based at least in part on the discharge rate and/or the run-time determined at blocks 302 and 303, respectively. As will be described in further detail below, the charge parameters can include the points at which various phases of the charging process are completed. Once the charge parameters are established, the parameters can be used to charge the battery (block 305). The parameters can be changed in response to changes in the therapy parameters, and/or can be checked and changed on a periodic, pre-established basis (block 306).

Figure 4:
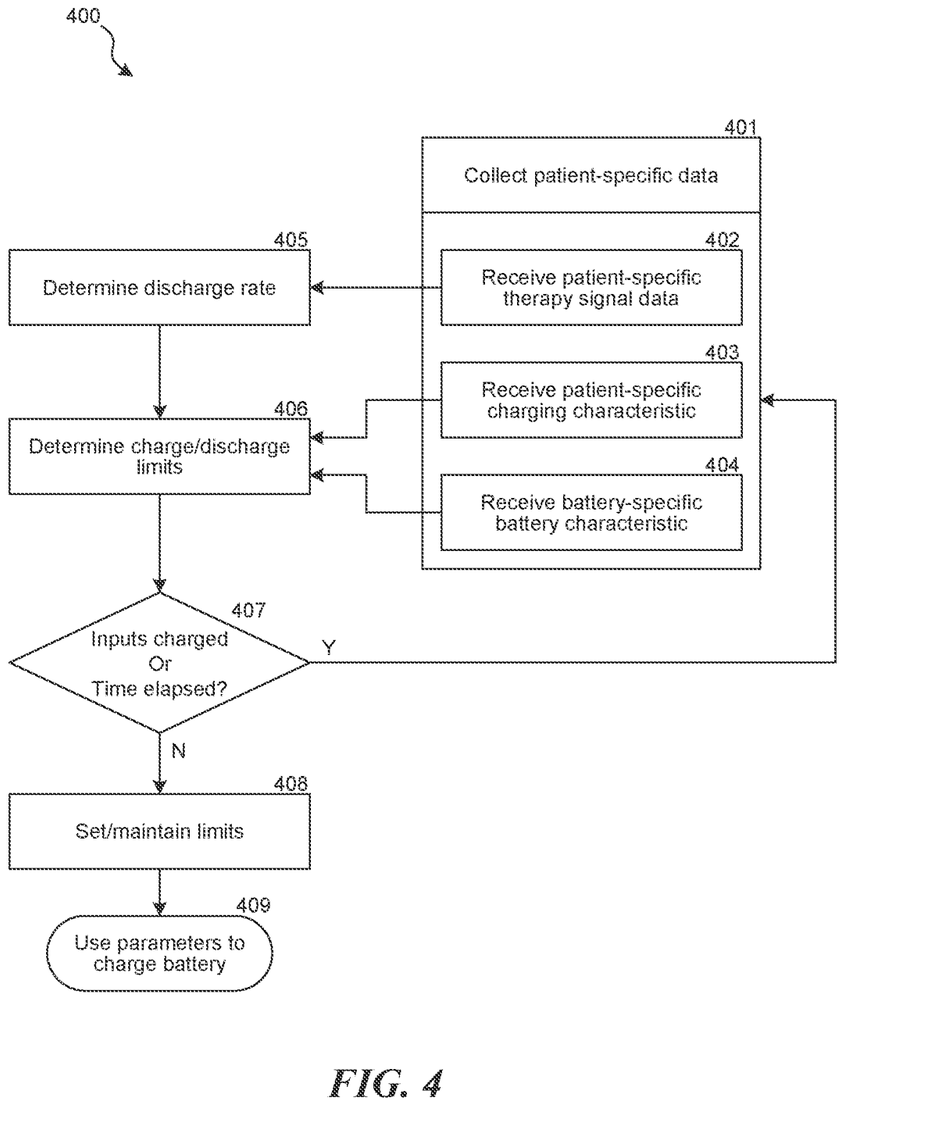
FIG. 4 is a flow diagram illustrating a representative process for establishing charging parameters in accordance with another embodiment of the present technology.

FIG. 4 is a flow diagram illustrating a representative process 400, with additional details provided for several of the process steps described above with reference to FIG. 3. For example, the process 400 can include collecting patient-specific data (block 401). As used herein, the term "patient-specific data" refers generally to data that varies from one patient to another. The term does not require that the data be unique for each patient. In a particular embodiment, the patient-specific data can be collected at the IPG itself. Accordingly, the IPG can include features for obtaining and at least temporarily storing patient-specific data. An advantage of collecting the patient-specific data at the IPG is that much, if not all, of the data may already be collected by and/or stored at the IPG during normal operations and accordingly, collecting the data is not expected to burden either the storage capacity or the memory capacity of the IPG. In another aspect of this embodiment, the steps for processing the data (in addition to collecting the data) can also be carried out at the IPG. An advantage of this feature is that the data can readily be transmitted to a battery charger during a recharge operation, without requiring an additional device.

The process of collecting patient-specific data can include receiving patient-specific therapy signal data (block 402), receiving at least one patient-specific charging characteristic (block 403) and/or receiving at least one battery-specific battery characteristic (block 404). The patient-specific therapy signal data (block 402) can include the signal delivery parameters in accordance with which the IPG generates and delivers electrical therapy signals to the patient. This information can be used to calculate The discharge rate can be calculated or otherwise determined, based at least in part on the foregoing patient-specific therapy signal data (block 405). For example, the frequency, pulse width, inter-pulse interval, amplitude, and/or duty cycle of the signal can be used to determine the rate at which charge is drawn from the battery. These foregoing signal delivery parameters are typically stored at the IPG (to be used by the IPG for generating the therapy signal) and are provided to the IPG via a physician and/or the patient.

The patient-specific therapy signal data can include other parameters, in addition to or in lieu of the foregoing signal delivery parameters. Such parameters can include impedances, e.g., impedances of one or more components or circuits used to deliver the electrical therapy signal to the patient. For example, a representative impedance value is the impedance of the electrical contacts (e.g., a bipolar pair of contacts), intervening patient tissue, and electrical wires in the lead or other signal delivery device.

The patient-specific charging characteristic (block 403) and the battery-specific battery characteristic (block 404) can be used alone or together to calculate the charge and/or discharge limits (block 406), e.g., in combination with the discharge rate determined at block 405. For example, the patient-specific charging characteristic can include historical data identifying how often the patient typically charges the battery and/or the consistency with which the patient adheres to a charging schedule. The battery-specific battery characteristic can include the age of the battery and/or the number of charging/discharging cycles undergone by the battery. For example, as a battery ages, the overall charge capacity of the battery typically decreases. As the number of charge/discharge cycles of the battery increases, the charge capacity of the battery also typically decreases. One or both of these factors can be considered in determining the charge and/or discharge limits in block 406.

At block 407, the process can include determining if the inputs described above (e.g., with reference to block 402, block 403, and/or block 404) have changed. If the inputs have changed, then new inputs are received at blocks 402, 403 and 404, respectively, and the discharge rate and charge/discharge limits are re-determined. Alternatively, the process can include re-determining the discharge rates and charge/discharge limits if a (pre-established) period of time has elapsed. For example, if the discharge rates and charge/discharge limits have not been re-determined for a period of several days, weeks or months, the process can automatically re-determined these quantities to ensure that they are up to date. Once it has been determined that the quantities are current, then the charge/discharge limits are set (or maintained) in block 408. These parameters are then used to charge the battery of the implantable pulse generator (block 409).

Figure 5:
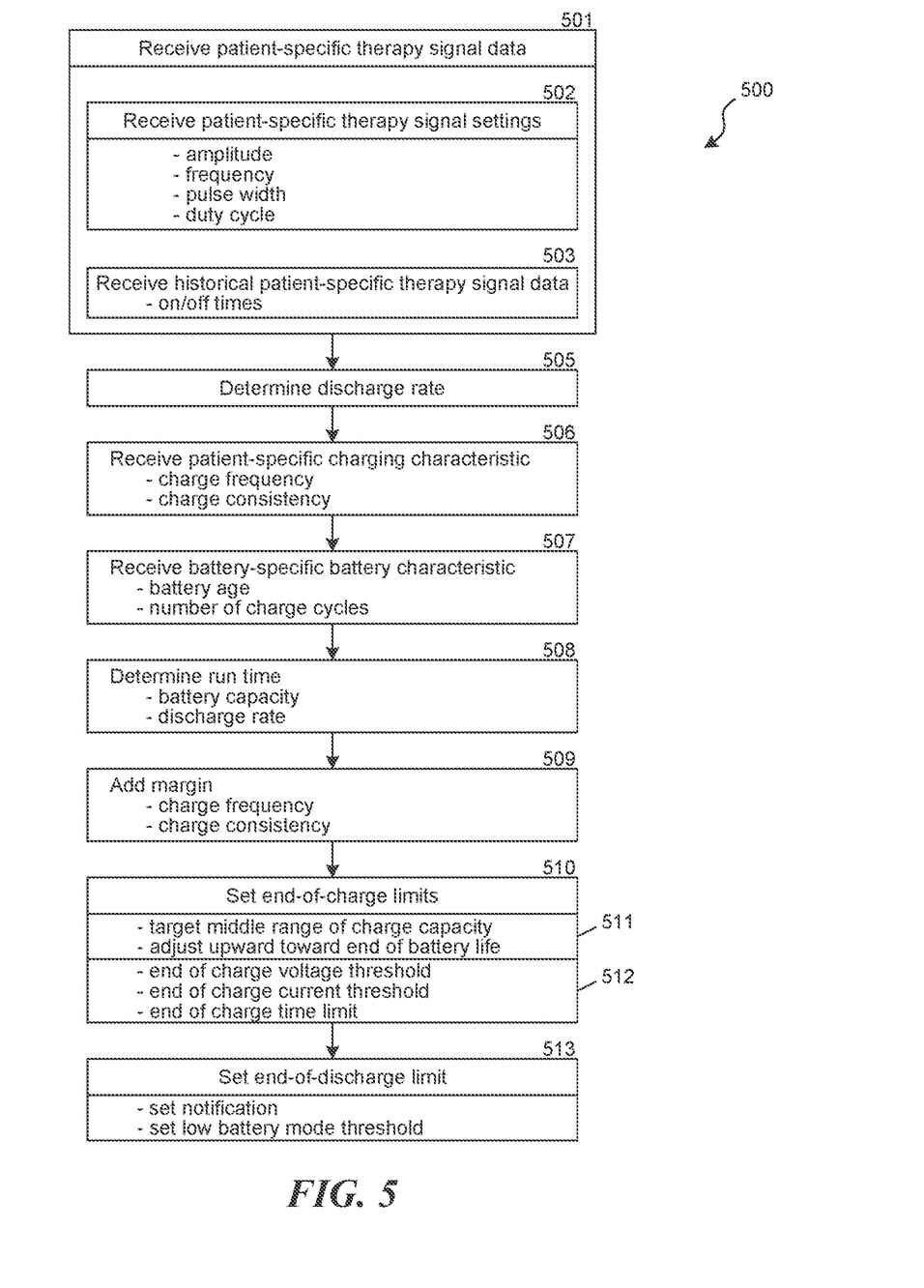
FIG. 5 is a flow diagram illustrating a process for establishing patient-specific charging and/or discharging parameters in accordance with still another embodiment of the present technology.

FIG. 5 illustrates a process 500 in accordance with still a further embodiment of the present technology, illustrating further details and specific parameters in accordance with which the determinations described above with reference to FIGS. 3 and 4 may be carried out. Block 501 includes receiving or retrieving patient-specific therapy signal data, which in turn can include receiving or retrieving patient-specific therapy signal settings (block 502) and/or receiving or retrieving historical patient-specific therapy signal data (block 503). The patient-specific therapy signal settings, as discussed above, can include amplitude, frequency, pulse width, inter-pulse interval and/or duty cycle. Other patient-specific variables associated with delivering the therapy include therapy signal circuit impedances. Depending upon the embodiment, at least some of the foregoing parameters may be selectable by the patient, by the practitioner, and/or by the manufacturer. For example, in a representative embodiment, the patient has control over the amplitude at which the therapy signal is delivered, within ranges set by the practitioner. The practitioner has control over the duty cycle and, in particular embodiments, the frequency, pulse width, and/or inter-pulse interval. In still further embodiments, the practitioner may have control over fewer of the foregoing parameters, with the remaining parameters being established by the manufacturer and/or being calculated based upon manufacturer presets in combination with the practitioner-selected parameters. For example, the inter-pulse interval can be calculated based upon the signal frequency and pulse width, and the frequency and/or pulse width can be set by the manufacturer or by the practitioner. In a typical process, the parameters set by the practitioner, and any parameters calculated or otherwise determined from such parameters, are established by the physician's programmer 217 (FIG. 2A) and transmitted wirelessly to the IPG.

In any of the foregoing embodiments, the patient-specific therapy signal settings can be sufficient to determine the discharge rate (block 505) alone, or in combination with the historical patient-specific therapy signal data identified at block 503. The historical data can include the on/off times historically selected by the patient at one or more patient-specific therapy signal settings. The on/off times can differ from the duty cycle (described above with reference to block 502) in that they may be selected by the patient, while the duty cycle may be selected by the practitioner. For example, the on/off time can include time periods when the patient turns the IPG-generated signal off, e.g., when particular activities engaged in by the patient are not benefited from receiving the signal. Unlike the duty cycle, which is typically repeated on a very regular schedule (e.g., with stimulation on for several seconds and off for several minutes), the on/off time may vary from day to day depending upon the activities engaged in by the patient.

At block 505, the process includes determining the discharge rate. As discussed above, this process can include determining the discharge rate based on the amplitude, frequency, pulse width, duty cycle, and/or on/off times by determining the energy associated with a signal having the signal characteristics described by the foregoing features. The discharge rate can take into account impedance values that may vary from patient to patient.

At block 506, the process includes receiving or retrieving patient-specific charging characteristics. Representative charging characteristics include a frequency with which the patient has historically charged the battery, a duration for which the patient charges the battery when the battery is charged, and/or a consistency with which the patient charges the battery. In particular embodiments, block 506 can include receiving a patient-specific charging characteristic that includes a charging interval value based at least in part on multiple prior intervals between charging events for the battery.

At block 507, the process includes receiving or retrieving battery-specific battery characteristics. The battery characteristics can include the age of the battery, the number of charge cycles undergone by the battery, the total amount of charge delivered by the battery (e.g., over many charge cycles), and/or other aspects of the battery that may vary from one patient's IPG to another patient's IPG. For example, an older battery and/or a battery that has been charged and discharged many times will typically have a lower total charge capacity than a battery that is new and/or has undergone fewer charge/discharge cycles. The data corresponding to these characteristics can be stored at the IPG and updated periodically. For example, the IPG can store the manufacture date of the battery. Each time the battery is charged, the IPG can increment a battery charge counter. At block 508, the run time for battery is determined, based at least in part on at least one charging characteristic, battery characteristic, or other characteristics. Representative characteristics include battery capacity and/or discharge rate.

The foregoing characteristics can be used to determine a margin by which to adjust the overall run time for the battery (block 509). In general, the margin is selected to protect the patient from inadvertently discharging the battery below a level at which the implantable device can support delivering the therapy signal. For example, if the patient charges the battery frequently (or has a short charging interval between charges), the margin can be relatively small because the likelihood that the patient will fully discharge the battery is reduced. Conversely, if the patient charges the battery infrequently, the margin can be larger.

The margin determination can be based at least in part on the consistency with which the patient charges the battery (in addition to or in lieu of considering the frequency with which the patient charges), based on historical information collected at the IPG. For example, if the patient tends to charge frequently but is inconsistent and accordingly has a significant number of large intervals between charging, then the margin applied to the discharge rate can be increased. If the patient is consistent in his or her charging habits (e.g., reliably charging the battery every day or reliably charging the battery every week) then the margin can be decreased.

The margin determination can include the consistency of the charge period, in addition to or in lieu of the foregoing characteristics. For example, if the patient reliably charges the battery for a consistent period of time, the margin can be decreased. If instead, the patient sometimes charges the battery for a few minutes and other times for significantly longer periods of time, then the margin can be increased. In the illustrated embodiment, the margin is added to the run time. In other embodiments, a margin can be applied to other factors used to determine the battery charging/discharging parameters, e.g., the margin can be applied to the discharge rate.

At block 510, the process includes setting end-of-charge (EOC) limits. Block 511 identifies representative factors that are considered in calculating the overall EOC limits. Such factors include the desirable feature of targeting the middle range of the charge capacity of the battery. For example, rather than charging the battery to 100%, a representative charge limit can be set to be 70%, 80%, or 90% of the full capacity of the battery. In addition to or in lieu of the foregoing consideration, the EOC limit for the complete charge limit of the battery can be adjusted depending on factors including the age of the battery. In a particular embodiment, the overall charge limits are adjusted upwardly toward the end of the life of the battery. For example, toward the end of the life of the battery, the benefit of charging the battery to less than its full capacity may be outweighed by the benefit of utilizing the final remaining charge capacity of the battery, which can be accomplished by charging the battery to (or close to) its full capacity.

The foregoing EOC limits refer to the complete or overall charge of the battery. In block 512, intermediate charge parameters can also be determined as part of the overall process of setting the EOC limits. For example, when the battery is charged using a primarily constant current process, one EOC limit is the EOC voltage threshold. The EOC voltage threshold corresponds to the voltage at which the constant current process ceases and the remaining charge is carried out using a different process, e.g., a constant voltage process. Other representative EOC limits include an EOC current threshold, which can correspond to the minimum current (after the EOC voltage threshold has been surpassed) at which the battery is to continue charging. Once this limit has been reached, the battery is considered fully charged and the overall charging process is complete. Alternatively, the EOC current threshold can be replaced with a time limit. The time limit can correspond to the maximum charge time after the EOC voltage threshold has been surpassed. In other embodiments, the foregoing limits can be re-ordered and/or replaced with other suitable limits, e.g., if the battery is charged using a primarily constant voltage process.

In still further embodiments, the process can include setting an end-of-discharge (EOD) limit at block 513, in addition to or in lieu of setting EOC limits. For example, if the patient charges infrequently and/or has an inconsistent charging history, then the end-of-discharge limit can be set conservatively so as not to approach the end of the battery's capacity too closely. In any of these embodiments, the EOD limit can correspond to a point at which a notification is issued to the patient, and/or a point in time when a low battery or power savings mode is entered. In a low battery mode, certain functions of the IPG can be suspended to allow the therapy to continue being delivered until the patient is able to charge the batteries. For example, in a particular embodiment, the IPG can suspend all functions (e.g., signal delivery functions and telemetry functions) except a clock function. In a further aspect of this embodiment, the IPG automatically resumes the therapy program it was delivering in response to being recharged. This is unlike conventional systems that require the patient to manually turn the IPG on and/or manually re-start a therapy program after the IPG is recharged from a low battery or power savings mode or state.

One feature of at least of at least some of the foregoing embodiments is that the charging parameters for the battery of an implantable pulse generator can be tailored, adjusted, determined, calculated, set, or otherwise established in a manner that reflects patient-specific and/or battery-specific characteristics. An advantage of this arrangement is that it can extend the life of the battery and thereby reduce or even eliminate the need to replace the battery.

Another feature of at least some of the foregoing embodiments is that the processes for establishing and/or adjusting the charge and/or discharge parameters can be automated. An advantage of this feature is that it can reduce or eliminate any effort on the part of the patient and/or the practitioner and/or the company representative to achieve the benefits of tailored charge/discharge parameters. Still another advantage of the foregoing features is that, in particular embodiments, the patients perception of the consistency of the system can be improved. For example, by automatically providing and adjusting (as needed) the margins within which the IPG battery operates, the patient will be less likely to over-discharge the battery.

Figure 6:
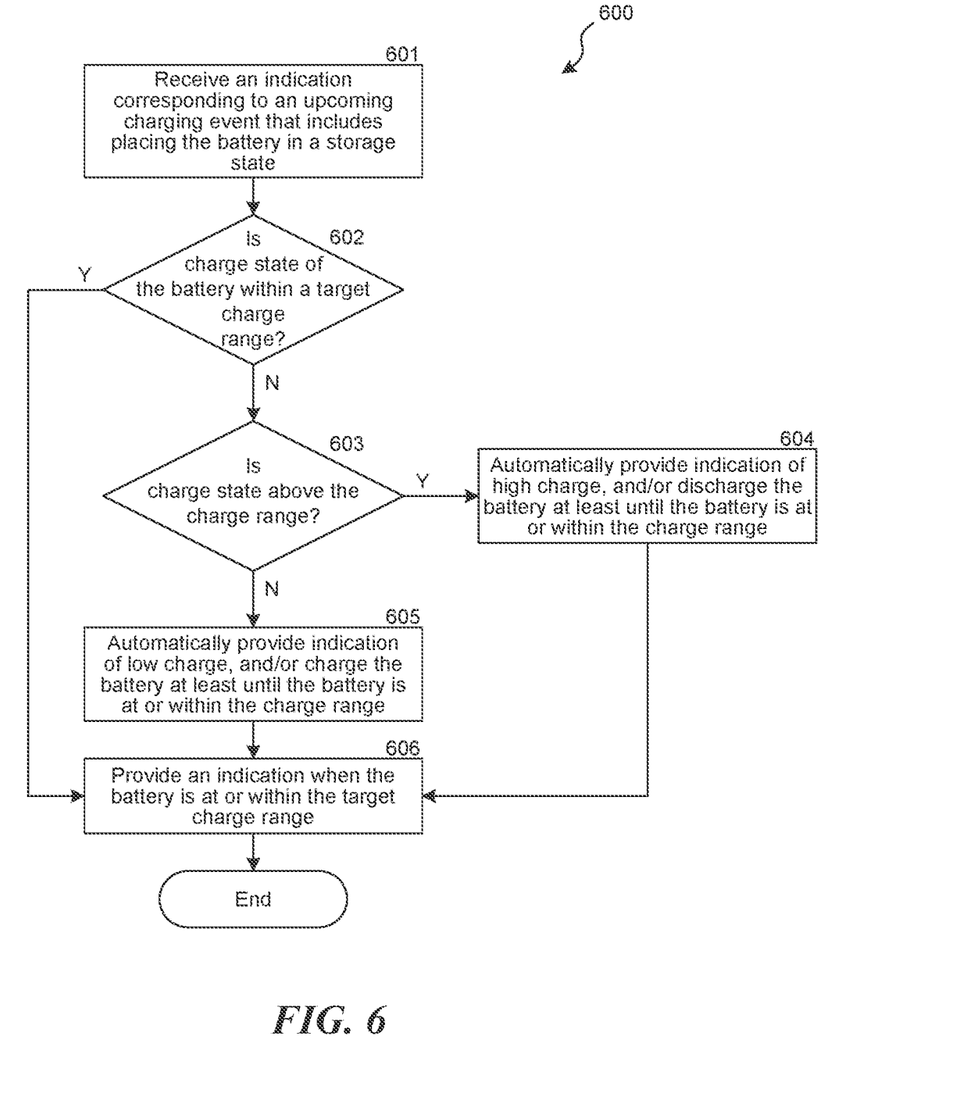
FIG. 6 is a flow diagram illustrating a process for placing a battery in a storage stage in accordance with yet another embodiment of the present technology.

FIG. 6 is a flow diagram illustrating a process for placing the battery of an implantable medical device in a storage state or stock mode, in accordance with a particular embodiment of the present technology. This technique can be used by the manufacturer to place the battery in a storage state prior to releasing the product for sale and/or distribution. In another embodiment, the process can be used by a practitioner (e.g., a representative of the manufacturer) to re-store a battery. For example, the battery may be re-stored if it has been taken out of storage and needs to be placed back into storage, or if the battery has exceeded its initial storage period and is to be placed back in storage. Typically, the battery is installed in the IPG at the time the storage state is entered, so both the IPG and the battery enter the storage state together.

The process 600 can include receiving an indication corresponding to an upcoming charging event that includes placing the battery in a storage state (block 601). For example, the indication can include a request by a manufacturer or practitioner to have the battery placed in a storage state. At block 602, the process includes determining if a charge state of the battery is within a target charge range. The target charge range is typically less than fully charged, but more than completely discharged. It is typically advantageous to store the battery with less than a full charge because storing a fully charged battery can increase the likelihood and/or extent to which the battery capacity fades.

At block 603, the process includes determining if the charge state of the battery is above the charge range. If so, then in block 604, the process can include automatically providing an indication to that effect, and/or automatically discharging the battery at least until the battery is at or within the charge range. The indication can include a graphical indication (at a graphical user interface) to an operator directing the operator to discharge the battery, and in other embodiments can include other types of indications.

If the charge state is below the charge range, then in block 605, the process can include automatically providing an indication to that effect, and/or automatically charging the battery at least until the battery is at or within the charge range. In block 606, the process includes optionally providing an indication when the battery is at or within the target charge range. At this point, the operator can store the battery and/or the IPG in which the battery is placed.

In other embodiments, the process 600 can include other inputs and/or processes. For example, the process 600 can include receiving an input corresponding to an amount of time the battery is to be stored. Based on this input, the process can include adjusting the target charge range. For example, if the battery is to be stored for a longer period of time, the process can charge the battery to a higher charge state. If the battery is to be stored for a relatively short period of time, the upper end of the charge range can be reduced. In any of these embodiments, an advantage of the foregoing features is that the features facilitate (and in at least some embodiments, automate) more precise charging for the battery, which can in turn reduce the likelihood that the battery will be overcharged or undercharged when it is placed in storage.

As part of entering the storage state or stock mode, the foregoing process can further include de-powering all the electronics of the IPG. For example, the process can include disabling or de-powering a MOSFET between the battery and all electronics of the IPG. In other embodiments, other elements or arrangements can be used to perform this function. In any of these embodiments, the MOSFET (or other interrupt device) can be re-powered, reset or otherwise re-configured to activate the previously de-powered electronics, in response to the presence of a charging coil, currents induced by the charging coil, and/or other aspect of a charging event.

From the foregoing, it will be appreciated that specific embodiments of the presently disclosed technology have been described herein for purposes of illustration, but that various modifications may be made without deviating from the disclosed technology. For example, some embodiments were described above in the context of particular therapy signals that produce pain relief without generating paresthesia. In other embodiments, other methodologies may be used to provide pain therapy to the patient, and in some instances, such methodologies may provide paresthesia-free pain relief.

In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 microseconds to about 333 microseconds, about 10 microseconds to about 166 microseconds, about 20 microseconds to about 100 microseconds, about 30 microseconds to about 100 microseconds, and about 30 microseconds to about 40 microseconds. Duty cycles can range from about 10% to about 100%, and in a particular duty cycle, signals are delivered for 20 seconds and interrupted for 2 minutes (an approximately 14% duty cycle). In other embodiments, these parameters can have other suitable values. For example, in at least some embodiments, the foregoing systems and methods may be applied to therapies that have frequencies outside the ranges discussed above (e.g., 1.5 kHz-100 kHz) but which also do not produce paresthesia. Representative pulse widths (which can be delivered at frequencies above or below 1.5 kHz, depending upon the embodiment) include pulse widths from 10-50 microseconds, 20-40 microseconds, 25-35 microseconds, 30-35 microseconds, and 30 microseconds.

In still further embodiments, techniques generally similar to those described above may be applied to therapies that are directed to tissues other than the spinal cord. Representative tissues can include peripheral nerve tissue and/or brain tissue.

In other embodiments, similar or identical techniques for handling charging and/or discharging processes and parameters may be used in the context of therapy parameters that generate paresthesia. Certain embodiments were described above in the context of spinal cord stimulators, and in other embodiments, generally similar or identical charge parameter selection techniques can be used for implantable devices that perform functions other than spinal cord stimulation. In several of the embodiments discussed above, retrieving, processing and/or other data functions are performed at the IPG. In other embodiments, at least some of the foregoing processes can be carried out by another component of the overall system, for example, a non-implantable component. In particular, certain processes can be carried out by a charger, based on data provided by the IPG at the time of charging.

Many of the foregoing processes include determining values, parameters, ranges and/or other quantities. As used herein, "determining" can include calculating, extrapolating, interpolating, applying table look up functions, estimating, and/or other suitable methods.

Certain aspects of the technology described in the context of particular embodiments may be combined or eliminated in other embodiments. For example, in some embodiments, the foregoing techniques can include using patient-specific therapy parameters, or battery-specific battery parameters, or a combination of both. In other embodiments, certain steps of an overall process can be re-ordered or eliminated. For example, blocks 603, 604, and 605 (discussed above with reference to FIG. 6) can be re-ordered so that determining if the charge state is below the charge range is performed first.

3.0 Additional Embodiments

In one embodiment, there is provided a method for establishing charge parameters for a battery-powered implantable medical device, comprising: receiving a patient-specific therapy signal parameter; based at least in part on the patient-specific therapy signal parameter, determining a discharge rate for a battery of the implantable medical device; based at least in part on the discharge rate, determining a therapy run time; and based at least in part on the run time, determining at least one battery charging parameter. The process of receiving the at least one patient-specific therapy signal parameter may be performed by the implantable medical device. The patient-specific therapy signal parameter may include a therapy signal amplitude, a therapy signal pulsewidth, or a therapy signal duty cycle. A representative method may further comprise receiving at least one charging characteristic, with the at least one charging characteristic including at least one of a battery-specific battery characteristic or a patient-specific charging characteristic; and based at least in part on the at least one charging characteristic and the discharge rate, determining a run time for the implantable medical device. The patient-specific charging characteristic can include a patient-specific charging interval, a patient-specific charging frequency, and/or a patient-specific charging consistency. The battery-specific battery characteristic can include an age of the battery, or a number of charging cycles undergone by the battery. The at least one charging parameter can include an end of charge limit, which can in turn include a voltage limit at which a constant current phase of a charging process ceases.

In another embodiment, there is provided a method for programming a battery-powered implantable medical device, comprising: programming the implantable medical device with instructions that, when executed: receive at least one patient-specific therapy signal parameter; direct a patient therapy signal to a signal delivery device in accordance with the at least one patient-specific therapy signal parameter; based at the least on the at least one patient-specific therapy signal parameter, determine a discharge rate for a battery of the implantable medical device; based at least in part of the discharge rate, determine a therapy run time; and based at least in part on the run time, determine at least one battery charging parameter.

In another embodiment, there is provided an implantable medical device, comprising: an implantable housing; and a pulse generator carried by the housing, the pulse generator being programmed with instructions that, when executed: receive at least one patient-specific therapy signal parameter; direct a patient therapy signal to a signal delivery device in accordance with the at least one patient-specific therapy signal parameter; based at least on the at least one patient-specific therapy signal parameter, determine a discharge rate for a battery of the implantable medical device; based at least in part on the discharge rate, determine a therapy run time; and based at least in part on the run time, determine at least one battery charging parameter.

In yet another embodiment, there is provided a method for charging a battery of an implantable medical device, comprising receiving an indication corresponding to an upcoming charging event that includes placing the battery in a storage state; determining if a charge state of the battery is within a target charge range; if the charge state is above the charge range, (a) automatically discharging the battery at least until the battery is at or within the charge range, or (b) automatically providing an indication that the battery is to be discharged prior to storage, or both (a) and (b); and if the charge state is below the charge range, (c), automatically charging the battery at least until the battery is at or within the charge range or (d) automatically providing an indication that the battery is to be charged, or both (c) and (d).

Implantable medical devices in accordance with still further embodiments comprise: an implantable housing; and a pulse generator carried by the housing, the pulse generator being programmed with instructions that, when executed, receive an indication corresponding to an upcoming charging event that includes placing the battery in a storage state; determine if a charge state of the battery is within a target charge range; if the charge state is above the charge range, (a) automatically provide an indication that the battery is to be discharged prior to storage, or (b) automatically discharge the battery at least until the battery is at or within the charge range, or both (a) and (b); and if the charge state is below the charge range, (c) automatically provide an indication that the battery is to be charged, or (d) automatically charge the battery at least until the battery is at or within the charge range, or both (c) and (d).

While advantages associated with certain embodiments of the disclosed technology have been described in the context of those embodiments, other embodiments may also exhibit such advantages, and not all embodiments need necessarily exhibit such advantages to fall within the scope of the present technology.

To the extent that any of the foregoing patents, published applications, and/or other materials incorporated herein by reference conflict with present disclosure, the present disclosure controls.

I claim:

1. An implantable medical device, comprising:
   an implantable housing;
   a battery; and
   a pulse generator carried by the housing and coupled to the battery, the pulse generator being programmed with instructions that, when executed:
      receive an indication corresponding to an upcoming charging event that includes placing the battery in a storage state;
      in response to receiving the indication and before placing the battery in the storage state, determine if a charge state of the battery is within a target charge range; and
      if the determined charge state is above the charge range, (a) automatically provide an indication that the battery is to be discharged prior to storage, or (b) automatically discharge the battery prior to storage at least until the battery is at or within the charge range, or both (a) and (b); and
      if the determined charge state is below the charge range, (c) automatically provide an indication that the battery is to be charged prior to storage, or (d) automatically charge the battery prior to storage at least until the battery is at or within the charge range, or both (c) and (d).

2. The device of claim 1 wherein the pulse generator includes circuitry configured to generate a therapy signal, and wherein the system further comprises:
   an interrupt device coupled between the circuitry and the battery, the interrupt device being configured to interrupt power from the battery to the circuitry after the charge state of the battery is determined, the interrupt device being configured to restore power from the battery to the circuitry in response to a charging event.

3. The device of claim 1 wherein the target charge range corresponds to a charge state less than fully charged and more than fully discharged.

4. The device of claim 1 wherein the instructions, when executed, cause the battery to enter the storage state and decouple from at least a portion of electronics of the pulse generator.

5. The device of claim 1 wherein the instructions, when executed:
   receive an input corresponding to an amount of time the battery is to be stored in the storage state; and
   based on the input, adjust the target charge range,
   wherein a longer amount of storage time correlates to a target charge range having higher values.

6. The device of claim 1 wherein the instructions, when executed:
   monitor the charge state of the battery as the battery is charging or discharging;
   if the battery is charging, (e) cease charging the battery once the charge state is within the target charge range, or (f) provide an indication that the battery is to cease charging the battery once the charge state is within the target charge range, or (e) and (f); and
   if the battery is discharging, (g) ceasing discharging the battery once the charge state is within the target charge range, or (h) provide an indication that the battery is to cease discharging the battery once the charge state is within the target charge range, or (g) and (h).

7. An implantable medical device, comprising:
   an implantable housing;
   a battery; and
   a pulse generator carried by the housing and coupled to the battery, the pulse generator being programmed with instructions for placing the battery in a storage state, the instructions to be implemented when the implantable housing is not implanted in a patient, wherein the instructions, when executed in response to a user request to place the battery in the storage state:
   determine if a charge state of the battery is within a target charge range;
   if the determined charge state is above the charge range, (a) automatically provide an indication that the battery is to be discharged prior to storage, or (b) automatically discharge the battery prior to storage at least until the battery is at or within the charge range, or both (a) and (b); and
   if the determined charge state is below the charge range, (c) automatically provide an indication that the battery is to be charged prior to storage, or (d) automatically charge the battery prior to storage at least until the battery is at or within the charge range, or both (c) and (d).

\* \* \* \* \*